US011452529B1

(12) United States Patent
Arona et al.

(10) Patent No.: US 11,452,529 B1
(45) Date of Patent: Sep. 27, 2022

(54) SURGICAL CLAMP

(71) Applicants: Audrey Arona, Duluth, GA (US);
Peter Van Winslett, Bessemer, AL (US)

(72) Inventors: Audrey Arona, Duluth, GA (US);
Peter Van Winslett, Bessemer, AL (US)

( * ) Notice: Subject to any disclaimer, the term of this patent is extended or adjusted under 35 U.S.C. 154(b) by 0 days.

(21) Appl. No.: 16/700,830

(22) Filed: Dec. 2, 2019

Related U.S. Application Data

(60) Provisional application No. 62/774,257, filed on Dec. 2, 2018.

(51) Int. Cl.
A61B 17/122 (2006.01)
A61B 17/28 (2006.01)
A61B 17/12 (2006.01)

(52) U.S. Cl.
CPC .......... *A61B 17/122* (2013.01); *A61B 17/282* (2013.01); *A61B 2017/12004* (2013.01); *A61B 2017/2837* (2013.01)

(58) Field of Classification Search
CPC .............. A61B 17/282; A61B 17/2812; A61B 2017/2837; A61B 17/122; A61B 17/2833; A61B 17/2841; A61B 17/28; A61B 17/2804; A61B 17/2816; A61B 2017/12004; A61B 2017/2825; A61B 2017/2829
See application file for complete search history.

(56) References Cited

U.S. PATENT DOCUMENTS

| 3,209,753 | A | | 10/1965 | Hawkins et al. | |
| 3,646,939 | A | | 3/1972 | Sklar | |
| 3,742,587 | A | | 7/1973 | Sklar | |
| 3,840,014 | A | * | 10/1974 | Ling | A61B 17/025 606/90 |
| 5,059,198 | A | | 10/1991 | Gimpelson | |
| 5,207,702 | A | | 5/1993 | Pearl | |
| 5,499,997 | A | * | 3/1996 | Sharpe | A61B 17/221 606/205 |
| 2007/0219582 | A1 | | 9/2007 | Brunelle et al. | |
| 2009/0105720 | A1 | | 4/2009 | Boone | |
| 2009/0264897 | A1 | * | 10/2009 | Wohl | A61B 17/24 606/110 |
| 2010/0152789 | A1 | | 6/2010 | Dell'Oca | |
| 2012/0143241 | A1 | * | 6/2012 | Ray | A61B 17/062 606/205 |
| 2016/0331408 | A1 | | 11/2016 | Benson et al. | |

FOREIGN PATENT DOCUMENTS

DE 202015105712 U1 * 1/2016 ......... A61B 17/2841

* cited by examiner

*Primary Examiner* — Katherine H Schwiker
(74) *Attorney, Agent, or Firm* — Barry E. Kaplan

(57) ABSTRACT

The subject matter of the present disclosure relates, in various embodiments, to a surgical clamp that holds tissue steady, without tearing; and, at the same time, that provides a tamponade effect to affected blood vessels, so that, once the surgical clamp is released, minimal (if any) bleeding occurs. Pressure-transmitting jaws disposed at a distal end of the surgical clamp form approximately flat, cooperating, confronting surfaces. In use and operation, the jaws act to pinch tissue therebetween, providing appropriate directed pressure to blood vessels within the jaws, so that bleeding is minimized, stopped, and/or prevented.

19 Claims, 5 Drawing Sheets

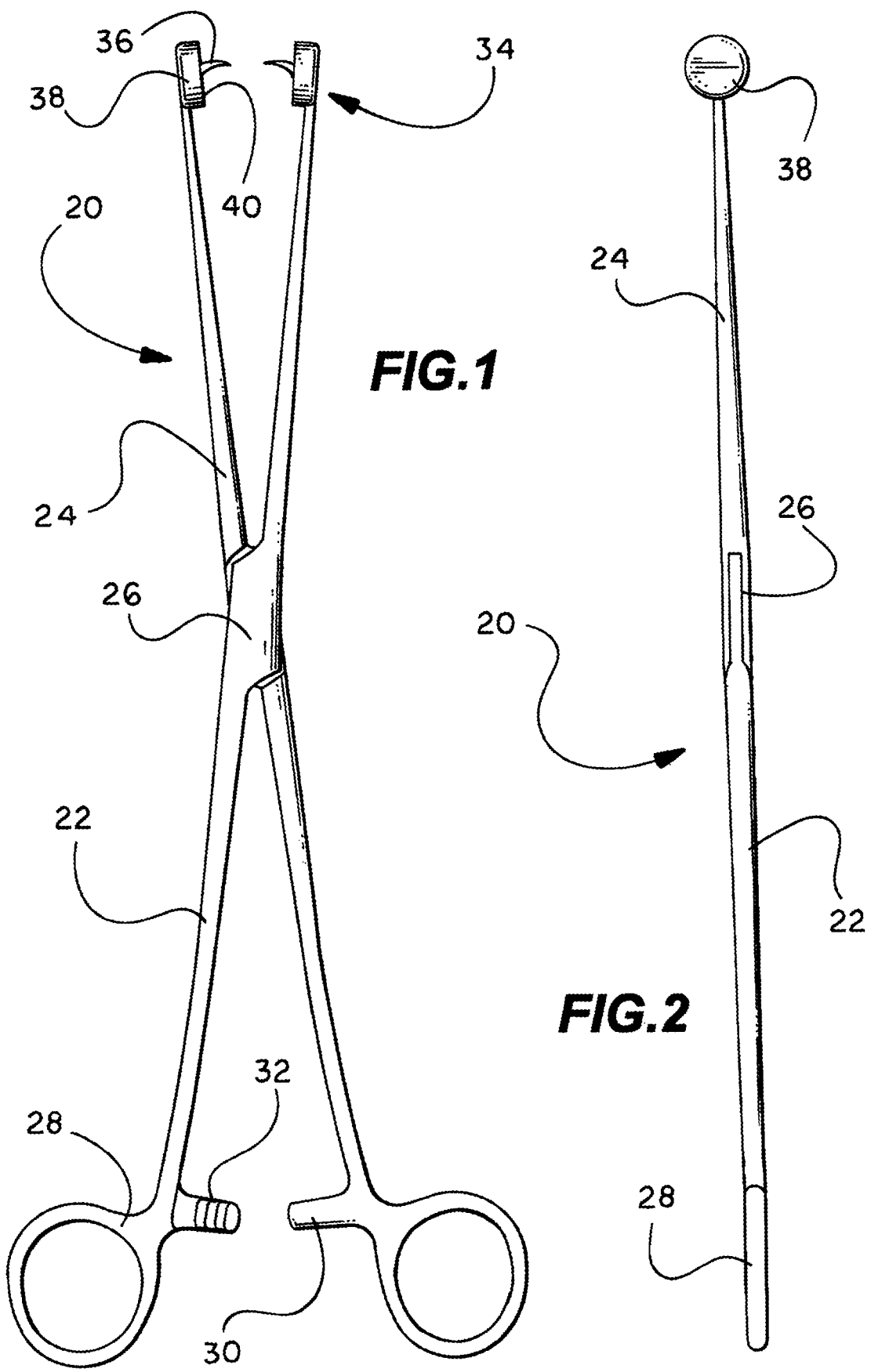

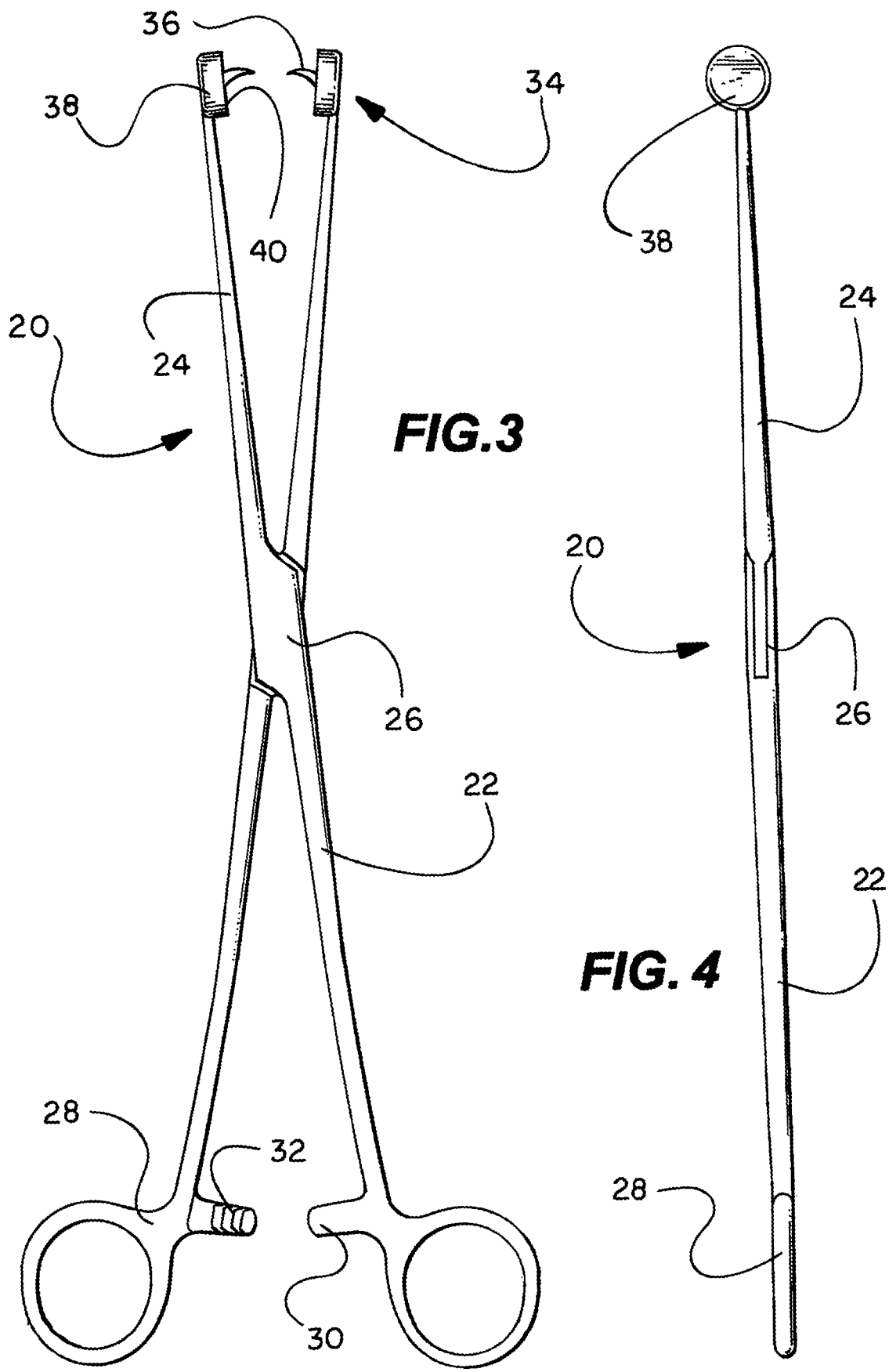

SURGICAL CLAMP

CROSS-REFERENCE TO RELATED APPLICATION

The present Application is a United States Non-Provisional Patent Application, which, pursuant to 35 U.S.C § 119(e), claims benefit of and priority to U.S. Provisional Patent Application Ser. No. 62/774,257, filed on Dec. 2, 2018, also entitled, "Surgical Clamp," and which is incorporated in its entirety herein by reference.

TECHNICAL FIELD

The subject matter of the present disclosure relates, generally, to surgical clamps. More particularly, the subject matter of the present disclosure relates to a surgical clamp in combination with a tenaculum forceps-type instrument for use during a surgical procedure for holding tissue steady without tearing, while providing a tamponade effect to blood vessels so that, once said clamp is released, minimal (if any) bleeding occurs.

BACKGROUND

A tenaculum is a type of surgical instrument, usually classified as a type of forceps. A tenaculum consists, typically, of a pair of confronting, slender, sharply-pointed prongs or hooks attached to a long handle. Often, the handle of a tenaculum is similar in structure and design to that of a surgical hemostat clamping instrument, which has handles that can be held in place by a locking mechanism spanning therebetween. The locking mechanism typically comprises a series of interlocking teeth, several associated with each handle, which allow the user to adjust the clamping force of the hemostat tips.

The tenaculum is used primarily in surgery for seizing and holding tissue in place, often while applying traction.

With regard to cervical and/or uterine procedures, holding the cervix in place usually requires the use of a tenaculum or a similar instrument. Disadvantageously, however, the sharp points of the tenaculum penetrate the blood vessels within the tissue, and cause continued bleeding upon release of the instrument. This bleeding requires surgical maneuvering to acquire hemostasis; and, often, acquiring hemostasis can take longer than the surgical procedure itself.

Clamps that traditionally cause and/or result in reduced tissue trauma, such as ring forceps or Allis clamps, cannot adequately hold the tissue under traction. As a result, use of such clamps can cause tearing of the tissue the clamp is intended to hold. As well, such clamps can cause lacerations, which then require sutures to achieve hemostasis.

Accordingly, there is a need for a surgical clamp that will hold tissue steady, without tearing; and, at the same time, that will provide a tamponade effect to affected blood vessels, so that, once the surgical clamp is released, minimal (if any) bleeding occurs. Such a surgical clamp would minimize bleeding-type complications; and would, accordingly, minimize or eliminate the extended surgical time required to obtain hemostasis. By avoiding bleeding in the first instance, such a surgical clamp would decrease the need for use of hemostasis methods and materials, such as, by non-limiting example, Monsels solution, silver nitrate, and suturing. As well, by minimizing surgical times, such a surgical clamp would reduce extended anesthesia time for the patient.

Accordingly, it is to the disclosure of such an improved surgical clamp that the present, within disclosure is directed.

SUMMARY

The subject matter of the present disclosure relates, in various embodiments, to solving the above-described need by providing, in various embodiments, a surgical clamp for use during a surgical procedure. The disclosed surgical clamp holds tissue steady without tearing, while providing a tamponade effect to blood vessels so that, once said clamp is released, minimal (if any) bleeding occurs. Accordingly, the above-described problems that were identified with regard to the prior art devices may be mitigated and/or largely solved by use of the present surgical clamp.

According to some embodiments, and/or in various embodiments, a surgical clamp according to the present disclosure may provide, at a distal, hook bearing end thereof, pressure plates comprising, on inside surfaces thereof, confronting, pressure-transmitting jaws. The hooks of the instant surgical clamp penetrate or otherwise protrude from the inside surface of the respective, corresponding jaw. The jaws act to pinch tissue therebetween, providing appropriate, directed pressure to blood vessels within the jaws, so that bleeding, such as may be caused or induced by the hooks, is minimized, stopped, and/or prevented.

In some embodiments, a surgical clamp according to the present disclosure does not close all the way; rather, the sharply-pointed distal ends of the hooks pass by each other and terminate in a full closure position when each touches and/or abuts the confronting surface of the opposing jaw.

In some embodiments, and/or in various embodiments, a surgical clamp according to the present disclosure may be formed of multi-piece construction, such as described hereinbelow, or it may be formed, in whole or in part, as an integral, solid construction, such as by forging, casting, die stamping, machining, and/or the like, without limitation.

In to some embodiments, and/or in various embodiments, a surgical clamp according to the present disclosure may be provided in conventionally lockable form, or it may be provided in non-lockable form.

In some embodiments, and/or in various embodiments, a surgical clamp according to the present disclosure may be provided with essentially straight necks, or the necks thereof may be provided in any of a variety of curved forms.

According to some embodiments, and/or in various embodiments, the disclosed surgical clamp may be formed from stainless steel (e.g., surgical steel), titanium, tantalum, platinum, palladium, and/or the like, and/or their respective alloys. In some embodiments, and/or in various embodiments, the disclosed surgical clamp, and/or portions thereof, may be plated or otherwise formed with biologically inert surface materials and/or coatings so as to enhance performance and operational characteristics.

Although the subject matter of the present disclosure may find particular application with regard to cervical and/or uterine procedures, its use also and further may be extended to other types of surgeries wherein the disclosed functionality, including traction in association with tamponade effect, may be useful and/or desirable.

These, and other, features, advantages, and benefits shown by the various embodiments of a surgical clamp according to the present disclosure, and the related processes for creating them, as set forth within the present disclosure, will become more apparent to those of ordinary skill in the art after review of the following Detailed Description of Illustrative Embodiments and Claims in light of the accompanying drawing Figures.

BRIEF DESCRIPTION OF THE DRAWINGS

Accordingly, the within disclosure will be best understood through consideration of, and with reference to, the following drawing Figures, viewed in conjunction with the Detailed Description of Illustrative Embodiments referring thereto, in which like reference numbers throughout the various Figures designate like structure, and in which:

FIG. 1 depicts a front view of a surgical clamp according to the present disclosure, the surgical clamp shown in an open configuration;

FIG. 2 depicts a right side view thereof;

FIG. 3 depicts a back view thereof;

FIG. 4 depicts a left side view thereof;

Figure 5:
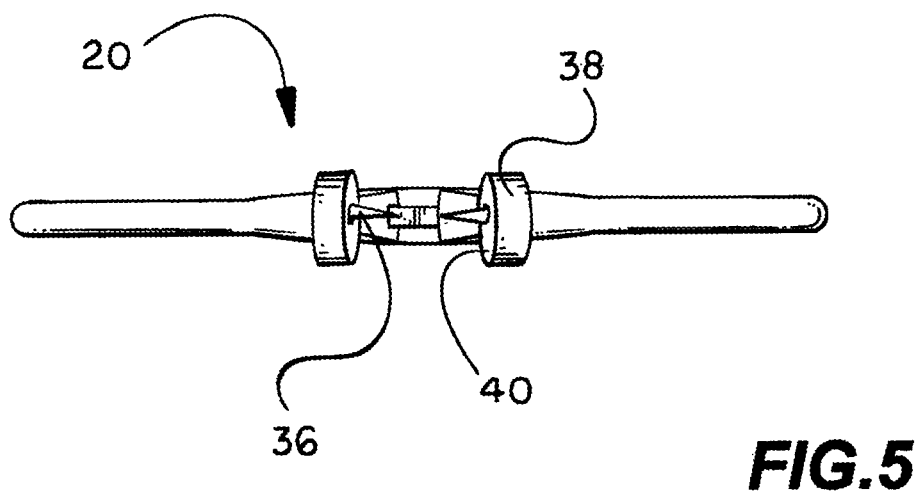
FIG. 5 depicts a top end view thereof.
Figure 6:
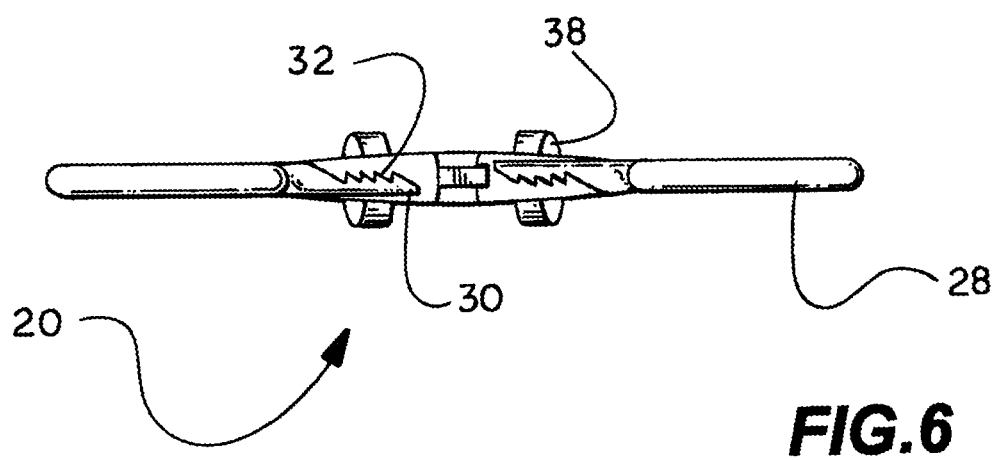
FIG. 6 depicts a bottom end view thereof.

It is to be noted that the drawing Figures presented are intended solely for the purpose of illustration and that they are, therefore, neither desired nor intended to limit the invention to any or all of the exact details of construction shown, except insofar as they may be deemed essential to the claimed invention.

DETAILED DESCRIPTION OF ILLUSTRATIVE EMBODIMENTS

In describing the several embodiments illustrated in the Figures, specific terminology is employed for the sake of clarity. The invention, however, is not intended to be limited to the specific terminology so selected, and it is to be understood that each specific element includes all technical equivalents that operate in a similar manner to accomplish a similar purpose. Additionally, in the Figures, like reference numerals and like description shall be used to designate corresponding elements, parts, and functionality throughout the several Figures.

Turning now to FIGS. 1-8, an embodiment of surgical clamp 20 according to the present disclosure is depicted. Surgical clamp 20 generally provides a tenaculum forceps-type instrument with modifications made at the prong or hook end, as described in detail hereinbelow. Surgical clamp 20 is intended for use during a surgical procedure for holding tissue steady without tearing, while providing a tamponade effect to blood vessels so that, once said clamp is released, minimal (if any) bleeding occurs.

Surgical clamp 20 may be formed from stainless steel (e.g., surgical steel), titanium, tantalum, platinum, palladium, and/or the like, and/or their respective alloys. Surgical clamp 20, and/or portions thereof, may be plated or otherwise formed with biologically inert surface materials and/or coatings so as to enhance performance and operational characteristics. So formed, surgical clamp 20 may be sterilized, as by autoclaving, according to conventional best-practices.

The body of surgical clamp 20 comprises shanks 22 and necks 24. Shanks 22 and necks 24 are interconnected via box lock-type joint 26. Shanks 22 are configured at distal ends thereof with ring handles 28, allowing a user to grasp, open, close, manipulate, and otherwise control surgical clamp 20.

In order to allow locking of clamp 20 in a user-selected position and/or configuration, shanks 22 further provide ratchets 30. Ratchets 30 comprise a plurality of confronting, ramp-like, cooperatively engaging teeth 32, which typically slide into interlocking engagement upon closure of clamp 20. Disengagement of ratchets 30 occurs upon manipulation of shanks 22 and ring handles 28 out of the plane of ratchet 30 closure, such as by flexure thereof in a plane generally perpendicular to clamp 20.

Necks 24 are configured at distal ends thereof with tips 34. Tips 34 are configured to form confronting, slender, sharply-pointed hooks 36. Best seen with reference to FIGS. 7 and 8, hooks 36 typically are ground or otherwise formed in configuration allowing the sharply-pointed distal ends thereof to pass by each other upon closure of clamp 20. Accordingly, the distal ends of hooks 36 may comprise a tapered, ramped, and/or other such surface configuration allowing this described functionality.

In order to effectuate the above-described, desired functionality of providing a tamponade effect to blood vessels so that, once surgical clamp 20 is released, minimal (if any) bleeding occurs, surgical clamp 20 is provided and configured with plates 38. Plates 38 comprise, on inside surfaces thereof, confronting, pressure-transmitting jaws 40.

Plates 38 preferably also are formed of stainless steel (e.g., surgical steel), titanium, tantalum, platinum, palladium, and/or the like, and/or their respective alloys. Plates 38 preferably are formed in disk-like, truncated cylindrical configuration; however, in other embodiments, plates 38 may take oval, hexagonal, or other shapes, so long as functionally consistent with the disclosure and purposes set forth herein.

Pressure-transmitting jaws 40 comprise approximately flat, cooperating, confronting surfaces. In use and operation, jaws 40 act to pinch tissue therebetween, providing appropriate directed pressure to blood vessels within jaws 40, so that bleeding is minimized, stopped, and/or prevented. Although jaws 40 preferably are smooth, in some embodiments, one or more surface texture or other grasp-enhancing feature may be provided.

Each plate 38 preferably is formed in singular form, and of a selected diameter and thickness. In some embodiments, each plate 38 may be approximately $3/8$ inches to $13/32$ inches (0.37 inches-0.41 inches) in diameter, with a selected thickness of approximately 10 gauge (0.13 inches-0.14 inches). Of course, other sizes and shapes are possible—and are functional, useful, and within contemplation of the present disclosure—so long as consistent with the use and function described herein.

Figure 9A:
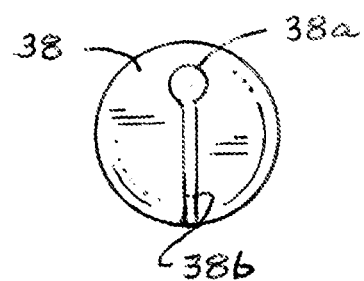
FIG. 9A depicts a back view thereof, further showing a hole and slot configuration as described herein.
Figure 9B:
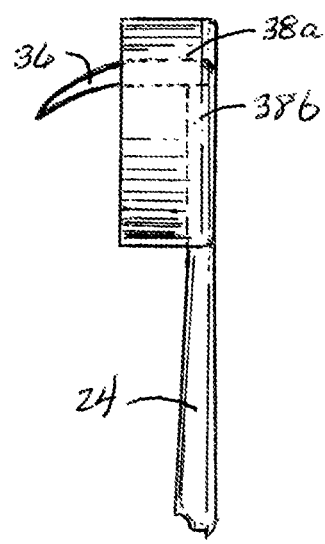
FIG. 9B depicts a partial side view of a top end thereof.

In some embodiments, and as best seen with reference to FIGS. 9A and 9B, each plate 38 is formed with a hole 38*a* or other-shaped opening off-set from the center of the plate or disk. Said hole 38*a* or opening may be formed by drilling, milling, punching, or the like. In some embodiments, each said hole 38*a* is approximately $1/8$ inch in diameter.

Each plate 38 further is formed, as by milling, key cutting, sawing, stamping, or other forming operation, with a slot or channel 38*b* in an outside surface thereof. Each slot or channel 38*b* runs from the respective hole or opening 38*a* to the outer edge of the disk, and is of size sufficient to fit therewithin the approximately parallel (sometimes tapered) sides of tip 34 of surgical clamp 20. In this configuration, hooks 36 protrude through plate 38 a selected distance, in some embodiments approximately $1/4$ inch.

Upon assembly of each plate 38 with respective tip 34, each plate 38 may be brazed or welded to form surgical clamp 20. Secondary operations, such as grinding, milling, or the like, may be used to flatten, smooth, or otherwise shape front and rear faces, as well as edges, of each plate 38, so as to remove excess materials, to finalize shape and dimension, and/or the like. Fixtures, holders, clamps, and the like may be used to stabilize, hold, and work plates 38, such as in forming the hole or opening 38a and the slot or channel 38b, in brazing and/or welding said plate to the respective tip, as well as in secondary operations to finalize the as-assembled instrument.

Figure 7:
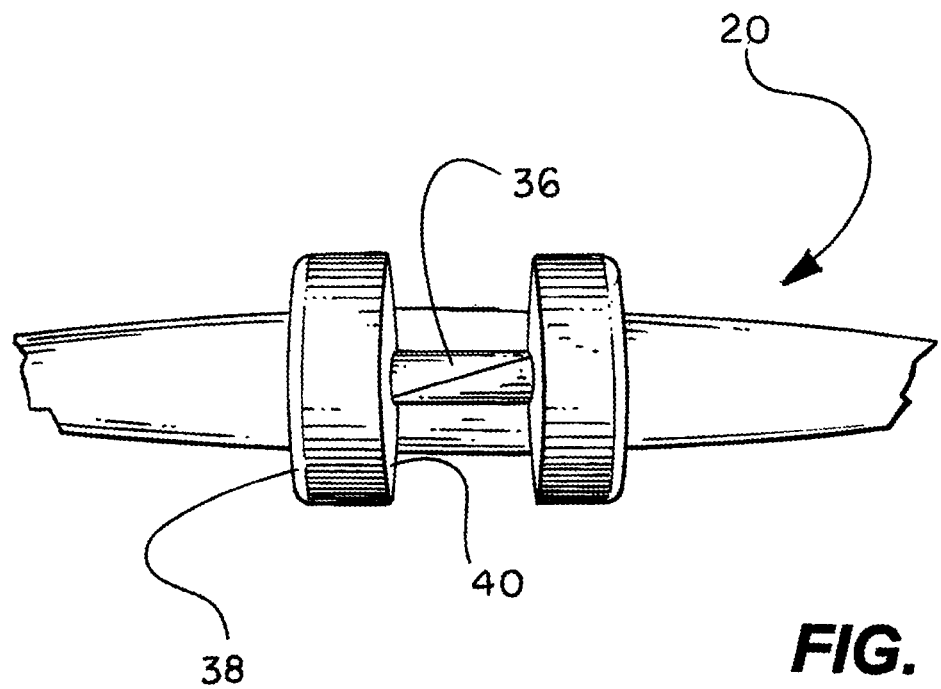
FIG. 7 depicts a partial (broken) top end view thereof in a closed configuration.
Figure 8:
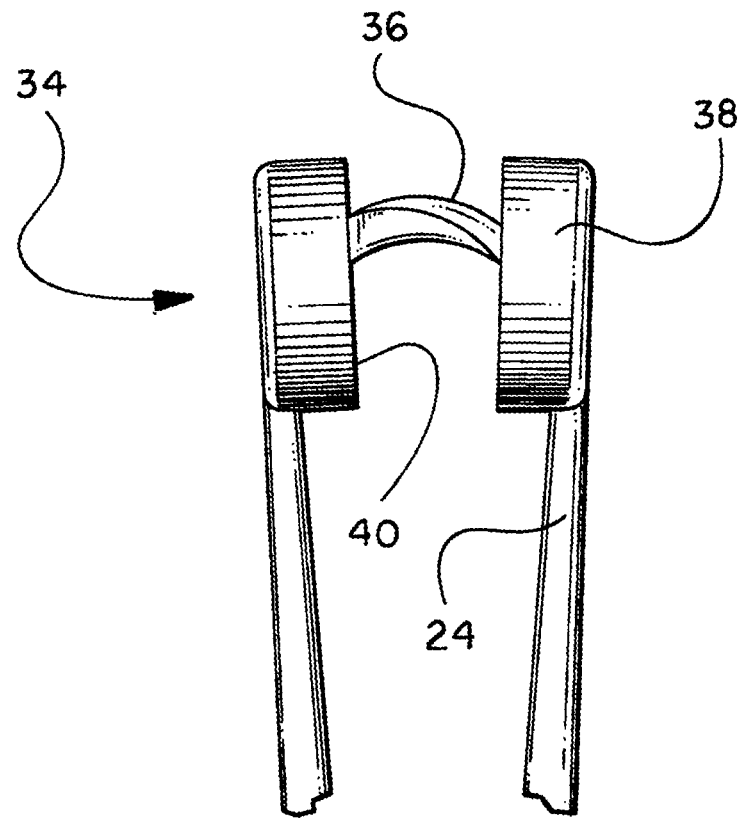
FIG. 8 depicts a partial (broken) side view of a top end thereof in a closed configuration.

As may best be seen with continuing reference to FIGS. 7 and 8, surgical clamp 20 does not close all the way; rather, sharply-pointed distal ends of hooks 36 pass by each other and terminate in full closure position when each touches and/or abuts the confronting surface of opposing jaw 40. In such closed position, and depending upon the selected, as-manufactured configuration of surgical clamp 20, confronting jaws 40 may be parallel to each other, or they may be slightly angled or canted vis-a-vis one another.

With benefit of the above-disclosure, it will be apparent to one of ordinary skill in the art that various alternative embodiments of surgical clamp 20 may be provided without departing from the scope, spirit, or nature of this disclosure.

For example, plates 38 may take the form of, and/or be configured as, a plurality of plates, stacked or otherwise disposed adjacent each other so-as to form, comprise, or adjust the thickness thereof.

Additionally, the depth of the aforedescribed channel or slot 38b may be adjusted to suit a specified design parameter and/or requirement.

Furthermore, surgical clamp 20 may be formed of multi-piece construction, such as has been described hereinabove, or it may be formed, in whole or in part, as an integral, solid construction, such as by forging, casting, die stamping, machining, and/or the like, without limitation.

Surgical clamp 20 may be provided in conventionally lockable form, as described herein; however, in other embodiments, it may be provided in non-lockable form.

Surgical clamp 20 may be provided with essentially straight necks 24, as described herein; however, in other embodiments, necks 24 may be provided in any of a variety of curved forms.

Surgical clamp 20 may be provided with only a single hook 36, such that it may operate by bearing against another suitably configured confronting plate and/or jaw that does not contain or carry a corresponding hook.

Surgical clamp 20 may be provided with any of a plurality of necks 24, or multi-part or branched configurations thereof, each carrying one or more confronting hooks 36 and/or plates 38.

It may now be seen that, advantageously, surgical clamp 20 will hold tissue steady, without tearing; and, at the same time, will provide a tamponade effect to affected blood vessels, so that, once the surgical clamp is released, minimal (if any) bleeding occurs. Configured as described herein, surgical clamp 20 minimizes bleeding-type complications; and accordingly, minimizes or eliminates the extended surgical time often required to obtain hemostasis. By avoiding bleeding in the first instance, surgical clamp 20 decreases the need for use of hemostasis methods and materials, such as, by non-limiting example, Monsels solution, silver nitrate, and suturing. As well, by minimizing surgical times, surgical clamp 20 may reduce extended anesthesia time for the subject patient.

For convenience of the reader, following is a summary of parts referenced in the written Specification and Drawings hereof:

| Part Number | Part Description |
| --- | --- |
| 20 | Surgical clamp |
| 22 | Shanks |
| 24 | Necks |
| 26 | Box lock joint |
| 28 | Ring handles |
| 30 | Ratchets |
| 32 | Teeth |
| 34 | Tips |
| 36 | Hooks |
| 38 | Plates |
| 40 | Jaws |

Having thus described exemplary embodiments of the subject matter of the present disclosure, it is noted that the within disclosures are exemplary only and that various other alternatives, adaptations, and modifications may be made within the scope and spirit of the present invention. Accordingly, the present subject matter is not limited to the specific embodiments as illustrated herein, but is limited only by the following claims.

What is claimed is:

1. A surgical clamp providing both traction and tamponade effect, said surgical clamp comprising:
   a shank;
   a neck;
   a ring handle disposed proximally from said shank; and
   a hook disposed distally from said neck;
   said hook carrying a pressure plate, such that said hook extends from and through an inside surface of said pressure plate;
   wherein, when said hook and said pressure plate confront a second surface associated with said surgical clamp, the surgical clamp may act to hold tissue therebetween steady without tearing, while providing a tamponade effect to adjacent blood vessels so that, once said clamp is released, minimal (if any) bleeding occurs.

2. The surgical clamp of claim 1, further comprising an interconnected second shank, a second neck, a second ring handle disposed proximally from said second shank, and a second hook disposed distally from said second neck, said second hook carrying a second pressure plate, such that said second hook extends from and through an inside surface of said second pressure plate.

3. The surgical clamp of claim 2, wherein an interconnection of said first and second shanks comprises a box lock joint.

4. The surgical clamp of claim 2, further comprising a plurality of cooperatively engaging ratchets.

5. The surgical clamp of claim 2, wherein said surgical clamp does not fully close such that distal ends of said hooks pass by each other and terminate in a closure position when one of said distal ends of said hooks abuts a confronting surface of an opposing pressure plate of said pressure plates.

6. The surgical clamp of claim 1, wherein said pressure plate comprises a disk-like structure.

7. The surgical clamp of claim 6, wherein said pressure plate comprises a truncated cylindrical configuration.

8. The surgical clamp of claim 1, wherein said pressure plate comprises an oval structure.

9. The surgical clamp of claim 1, wherein said pressure plate comprises a surface texture, grasp-enhancing feature.

10. The surgical clamp of claim 1, wherein said hook comprises a tapered surface configuration.

11. The surgical clamp of claim 1, wherein said pressure plate is approximately 0.37-0.41 inches in diameter.

12. The surgical clamp of claim 1, wherein said pressure plate comprises a thickness of approximately 10 gauge.

13. The surgical clamp of claim 1, wherein said pressure plate is formed with an opening that is off-set from the center of said pressure plate.

14. The surgical clamp of claim 13, wherein said pressure plate has a slot or channel formed on a second rearward or backside surface, said slot or channel running from said opening to an outer edge of said rearward or backside surface of said pressure plate, and which is of a size sufficient to fit therewithin a rearward portion of said hook.

15. The surgical clamp of claim 1, wherein said hook protrudes through an opening formed in said pressure plate approximately ½ inch.

16. A surgical clamp providing both traction and tamponade effect, said surgical clamp comprising:
   interconnected first and second shanks, first and second necks, first and second ring handles disposed proximally from each of said shanks, and first and second hooks disposed distally from each of said necks, each of said hooks carrying a pressure plate, such that each of said hooks extends through an opening formed in an inside surface of each of a corresponding one of said pressure plates;
   wherein, when said first hook and said first pressure plate confronts said second hook and said second pressure plate associated with said surgical clamp, the surgical clamp may act to hold tissue therebetween steady without tearing, while providing a tamponade effect to adjacent blood vessels so that, once the surgical clamp is released, minimal (if any) bleeding occurs.

17. The surgical clamp of claim 16, further comprising a box lock joint interconnection.

18. The surgical clamp of claim 16, further comprising a plurality of cooperatively engaging ratchets.

19. A surgical clamp providing both traction and tamponade effect, said surgical clamp comprising:
   interconnected first and second shanks, first and second necks, first and second ring handles disposed proximally from each of said shanks, and first and second hooks disposed distally from each of said necks, each of said first and second hooks carrying a pressure plate, such that each of said first and second hooks extends through an opening formed in an inside surface of each of a corresponding one of said pressure plates;
   each of said pressure plates comprising a truncated cylindrical configuration, wherein said pressure plate is approximately 0.37-0.41 inches in diameter, and wherein each of said pressure plates comprises a thickness of approximately 10 gauge;
   an interconnection joint; and,
   a plurality of cooperatively engaging ratchets;
   wherein, when said first hook and said first pressure plate confronts said second hook and said second pressure plate associated with the surgical clamp, the surgical clamp may act to hold tissue therebetween steady without tearing, while providing a tamponade effect to adjacent blood vessels so that, once the clamp is released, minimal (if any) bleeding occurs.

\* \* \* \* \*